(12) United States Patent
Havard et al.

(10) Patent No.: US 12,214,142 B2
(45) Date of Patent: *Feb. 4, 2025

(54) URINARY CATHETER

(71) Applicant: The Flume Catheter Company Limited, Surrey (GB)

(72) Inventors: John Havard, Surrey (GB); Roger Holmes, Surrey (GB)

(73) Assignee: The Flume Catheter Company Limited, Surrey (GB)

( * ) Notice: Subject to any disclaimer, the term of this patent is extended or adjusted under 35 U.S.C. 154(b) by 294 days.

This patent is subject to a terminal disclaimer.

(21) Appl. No.: 17/885,778

(22) Filed: Aug. 11, 2022

(65) Prior Publication Data

US 2022/0387751 A1 Dec. 8, 2022

Related U.S. Application Data

(63) Continuation of application No. 16/479,701, filed as application No. PCT/GB2018/050136 on Jan. 18, 2018, now Pat. No. 11,446,468.

(30) Foreign Application Priority Data

Jan. 20, 2017 (GB) ..................................... 1701027

(51) Int. Cl.
 *A61M 25/00* (2006.01)
 *A61M 25/04* (2006.01)
 *A61M 25/10* (2013.01)

(52) U.S. Cl.
 CPC ...... *A61M 25/0017* (2013.01); *A61M 25/007* (2013.01); *A61M 25/1002* (2013.01);
 (Continued)

(58) Field of Classification Search
 CPC .......... A61M 25/1002; A61M 25/0017; A61M 2025/1072; A61M 2210/1085;
 (Continued)

(56) References Cited

U.S. PATENT DOCUMENTS 3,438,375 A 4/1969 Ericson
3,811,448 A 5/1974 Morton
(Continued)

FOREIGN PATENT DOCUMENTS

AU 1103188 A 8/1988
CN 102908715 A 2/2013
(Continued)

OTHER PUBLICATIONS

American Heritage Dictionary Entry: fold. https://www.ahdictionary.com/word/search.html?q=fold. Accessed Nov. 5, 2024.*
(Continued)

*Primary Examiner* — Adam Marcetich
(74) *Attorney, Agent, or Firm* — Potomac Law Group, PLLC; Vincent M DeLuca

(57) ABSTRACT

A catheter comprising: a shaft (1) having a proximal end (2) and a distal end (3), the distal end terminating in a tip (4); a drainage opening (7) located at the distal end of the shaft, the drainage opening communicating with a drainage lumen (8) of the shaft; a balloon located at the distal end of the shaft, the balloon comprising a first region secured to the shaft, a second region secured to the shaft and an elastic-walled conduit extending between the first region and the second region, the elastic conduit extending over the tip.

20 Claims, 7 Drawing Sheets

(52) U.S. Cl.
CPC .... *A61M 25/1029* (2013.01); *A61M 25/1034* (2013.01); *A61M 25/1036* (2013.01); *A61M 25/04* (2013.01); *A61M 2025/1093* (2013.01); *A61M 2210/1085* (2013.01); *A61M 2210/1089* (2013.01)

(58) Field of Classification Search
CPC .. A61M 2025/1004; A61M 2025/1093; A61M 25/1036; A61M 2025/1065; A61M 2025/1086; A61M 2210/1089; A61M 25/0069; A61M 25/1038; A61M 2025/006; A61M 2025/1059; A61M 2025/1068
See application file for complete search history.

(56) References Cited

U.S. PATENT DOCUMENTS

| | | | |
|---|---|---|---|
| 3,889,686 A | | 6/1975 | Duturbure |
| 3,954,110 A | | 5/1976 | Hutchison |
| 4,222,384 A | | 9/1980 | Birtwell |
| 4,233,983 A | * | 11/1980 | Rocco .................. A61M 25/04 |
| | | | 604/97.01 |
| 4,351,342 A | | 9/1982 | Wiita et al. |
| 4,762,130 A | | 8/1988 | Fogarty et al. |
| 5,042,976 A | | 8/1991 | Ishitsu et al. |
| 5,250,029 A | | 10/1993 | Lin et al. |
| 5,308,325 A | * | 5/1994 | Quinn .................. A61J 15/0042 |
| | | | 604/174 |
| 5,401,241 A | * | 3/1995 | Delany ............. A61M 25/1002 |
| | | | 604/523 |
| 5,451,232 A | | 9/1995 | Rhinehart et al. |
| 5,776,047 A | * | 7/1998 | Fukunaga ........... A61M 60/295 |
| | | | 604/509 |
| 6,063,056 A | | 5/2000 | Engelberg |
| 10,195,394 B2 | | 2/2019 | Havard |
| 2002/0173816 A1 | | 11/2002 | Hung |
| 2003/0032963 A1 | | 2/2003 | Reiss et al. |
| 2005/0261663 A1 | * | 11/2005 | Patterson ............ A61M 25/008 |
| | | | 264/632 |
| 2006/0167406 A1 | | 7/2006 | Quinn |
| 2007/0185566 A1 | * | 8/2007 | Khitin ................ A61B 17/0057 |
| | | | 623/1.36 |
| 2007/0255209 A1 | * | 11/2007 | Crooms .............. A61J 15/0042 |
| | | | 604/104 |
| 2008/0071250 A1 | | 3/2008 | Crisp |
| 2008/0097300 A1 | | 4/2008 | Eskaros et al. |
| 2008/0221552 A1 | | 9/2008 | Leonard |
| 2009/0030370 A1 | | 1/2009 | Nishtala et al. |
| 2009/0221992 A1 | | 9/2009 | Hannon et al. |
| 2010/0234668 A1 | | 9/2010 | Roeder et al. |
| 2011/0040365 A1 | * | 2/2011 | Hirszowicz ............. A61F 2/958 |
| | | | 600/7 |
| 2011/0098683 A1 | | 4/2011 | Wiita et al. |
| 2011/0190737 A1 | | 8/2011 | Rocco |
| 2011/0295201 A1 | | 12/2011 | Degen |
| 2012/0059317 A1 | | 3/2012 | Michiyo et al. |
| 2012/0203210 A1 | | 8/2012 | Schanz et al. |
| 2013/0281926 A1 | | 10/2013 | Raux et al. |
| 2015/0005866 A1 | | 1/2015 | Komatsu et al. |
| 2015/0141917 A1 | * | 5/2015 | Tilson .................. A61F 2/2433 |
| | | | 604/103.09 |
| 2015/0359996 A1 | | 12/2015 | Arora et al. |
| 2016/0089254 A1 | | 3/2016 | Hopkinson et al. |
| 2018/0311483 A1 | | 11/2018 | Chin et al. |
| 2018/0361125 A1 | * | 12/2018 | Samuels ........... A61M 25/1002 |

FOREIGN PATENT DOCUMENTS

| | | |
|---|---|---|
| EP | 1142530 A1 | 10/2001 |
| GB | 2510497 A | 8/2014 |
| JP | 2012005786 A | 1/2012 |
| WO | 9200117 A1 | 1/1992 |
| WO | 2007/005734 A2 | 1/2007 |
| WO | 2010/046828 A1 | 4/2010 |
| WO | 2017/158081 A1 | 9/2017 |

OTHER PUBLICATIONS

Fold Definition & Meaning—Merriam-Webster. https://www.merriam-webster.com/dictionary/fold. Accessed Nov. 5, 2024.*
Conduit | meaning in the Cambridge English Dictionary. https://dictionary.cambridge.org/dictionary/english/conduit (2022).

* cited by examiner

URINARY CATHETER

This invention relates to urinary catheters.

Urinary catheters are used to assist or control the flow of urine from the bladder of a patient. When a patient needs to use a catheter for an extended period of time, they may use an indwelling urinary catheter. An indwelling urinary catheter has a tube which is introduced through the patient's urethra or directly via an abdominal incision (supra-pubic catheter). Once the distal tip of the catheter is in the bladder it is retained in position by means such as a balloon inflated within the bladder. A lumen extending through the catheter can then drain urine from the bladder.

A common design of indwelling urinary catheter is the Foley catheter. In the Foley catheter, the balloon is toroidal in shape and is located proximally of the catheter tip. A drainage opening which communicates with the lumen is located between the catheter tip and the balloon. Catheters of this design suffer from a number of problems. The tip of the catheter is exposed and can irritate the bladder wall. Material of the bladder wall can become drawn into the drainage opening, causing discomfort and mucosal damage. The drainage opening is spaced from the base of the bladder by the balloon, which prevents the bladder draining completely leading to a residual pool of urine that can become infected.

WO 2015/028786 discloses one approach to addressing at least some of these problems. It provides a urinary catheter having an inflatable balloon which extends over the tip of the catheter. WO 2007/005734 discloses another design of urinary catheter, in which the drainage opening extends proximally of the inflatable balloon.

There is a need for an improved design of urinary catheter.

According to one aspect of the present invention there is provided a catheter comprising: a shaft having a proximal end and a distal end, the distal end terminating in a tip; a drainage opening located at the distal end of the shaft, the drainage opening communicating with a drainage lumen of the shaft; a balloon located at the distal end of the shaft, the balloon comprising a first region secured to the shaft, a second region secured to the shaft and an elastic-walled and/or flexible-walled conduit extending between the first region and the second region, the elastic-walled conduit extending over the tip.

At least part of the first region may be located proximally of the drainage opening. At least part of the second region may be located proximally of the drainage opening.

At least a part of the balloon is in the form of an elongate tube. That part may comprise the elastic- and/or flexible-walled conduit.

The first region may be at one end of the tube and the second region may be at the other end of the tube.

The catheter may be such that: the balloon is in its uninflated state; the tube has lateral edges; the balloon comprises an outer layer defining the exterior of the balloon in its uninflated state; and the balloon is folded so that the lateral edges are located between the outer layer and the shaft of the catheter. In a state of the catheter prior to inflation and/or use, lateral edges of the conduit may be sandwiched between a central portion of the conduit and the shaft of the catheter, for example between the central portion of the conduit and a part of the catheter shaft that is any one or more of (i) a distal part of the shaft of the catheter, (ii) the tip of the catheter, and (iii) a lateral portion of the shaft of the catheter.

The first and second regions may overlap.

The first region and/or the second region may span an arc of greater than 90 degrees around the longitudinal axis of the catheter.

The first region and/or the second region may span an arc of greater than 180 degrees around the longitudinal axis of the catheter.

The catheter may comprise an inflation opening located at the distal end of the shaft. The inflation opening may communicate with an inflation lumen of the shaft and with the interior of the balloon.

The balloon may comprise two walls where it extends over the tip. The region between the walls may communicate with the inflation opening. There may be additional layers of elastic or inelastic material externally of the balloon.

The balloon may be configured such that when inflated an exterior wall of the balloon is located distally of and spaced from the tip of the catheter.

The balloon may be configured such that when inflated an interior wall of the balloon bears against the tip of the catheter.

The drainage opening may be located on a side of the catheter shaft. The balloon may be configured such that, when it is inflated, regions of the exterior of the balloon are located laterally outward of that side of the catheter shaft on either side of the drainage opening.

The balloon may be configured such that, when it is inflated, regions of the exterior of the balloon are located radially outward of the catheter shaft proximally of the most proximal part of the drainage opening.

The balloon may be configured such that, when it is inflated, regions of the exterior of the balloon extend radially outward with respect to the longitudinal axis of the catheter shaft around the majority of the or each drainage opening.

The balloon may be formed of a material that has a tendency to adhere to itself.

The ratio of (i) the mean diameter of the catheter shaft immediately distal of the drainage opening to (ii) the distance from the most distal part of the first region to the tip of the catheter may be in the range from 0.8:1 to 3:1 alternatively from 1:1 to 2.5:1, alternatively from 1.2:1 to 2:1, alternatively from 1:2 to 2:1.

The material forming the wall of the balloon may be of uniform elasticity across its area, or of non-uniform elasticity across its area. The wall of the balloon may comprise one or more thickened regions such as ribs for reducing the elasticity of the wall adjacent thereto.

The balloon may be secured to the shaft at the first and second regions by a mechanical fixing clamping the balloon to the shaft. The mechanical fixing may, for example, be a collar surrounding the shaft. The balloon may in addition be attached to the shaft by adhesive.

The balloon may be configured so that when the balloon is inflated, a wall of the balloon facing the tip is spaced from the tip. The drainage opening may open distally from the tip.

When the balloon is in its uninflated state, material of the balloon may be stowed in the drainage lumen.

According to a second aspect of the present invention there is provided a method for manufacturing a catheter comprising: providing a shaft having a proximal end and a distal end, the distal end terminating in a tip, a drainage opening located at the distal end of the shaft, the drainage opening communicating with a drainage lumen of the shaft and an inflation opening located at the distal end of the shaft, the inflation opening communicating with an inflation lumen of the shaft; providing an elastic-walled conduit having an access opening to the interior thereof; securing a wall of the conduit to the shaft around the inflation opening; introducing a tool through the access opening; piercing the wall of the conduit with the tool at the location of the inflation opening; and closing the access opening.

The method may further comprise: locating the elastic-walled conduit over the tip of the catheter; and securing a wall of the conduit to the shaft on the opposite side of the shaft to the inflation opening.

The conduit may be attached to the shaft of the catheter such that the interior of the of the conduit communicates in a fluid-tight manner with the inflation lumen. The conduit may be fluid-tight except for an aperture to the inflation opening A valve may be located in the inflation lumen. The valve may be capable of resisting flow of fluid from the distal end of the shaft to the proximal end of the shaft.

The catheter may be a urinary catheter. The catheter may be an indwelling urinary catheter.

Parts of the elastic-walled conduit may be inelastic.

The conduit may be located distally of the tip. In an inflated state of the balloon a wall of the conduit immediately distal of the tip may contact or may be spaced from the tip. When the balloon is in an inflated state, the tip may be in contact with material of the balloon or may be exposed.

The conduit may be integral with the first and second regions.

The shaft may be an elongate shaft.

The present invention will now be described by way of example with reference to the accompanying drawings. In the drawings.

Figure 1:
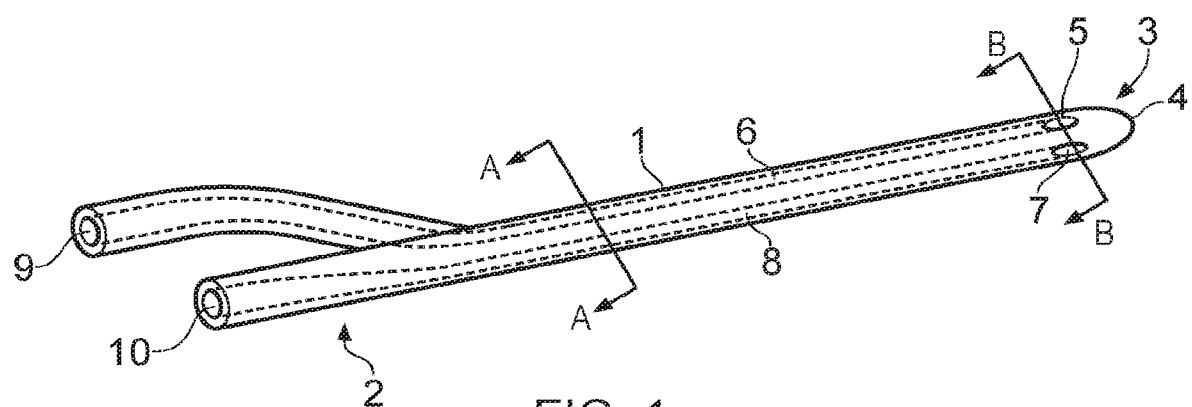
FIG. 1 is an isometric view of a urinary catheter without a balloon in place.
Figure 2:
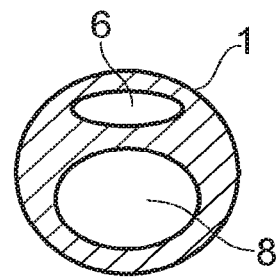
FIG. 2 is a cross-section of the shaft of the catheter of FIG. 1 on line A-A.

FIG. 1 shows a urinary catheter having a shaft 1. The catheter shaft has a proximal end 2. The proximal end is intended to sit outside the body when the catheter is in use. The catheter has a distal end 3. The distal end is intended to sit in the bladder of a user when the catheter is in use. The distal end of the catheter terminates in a tip 4. Two openings are defined in the distal end of the catheter. An inflation opening 5 is intended for inflating a balloon which can be attached to the catheter. The inflation opening communicates with an inflation lumen 6 which runs along the shaft. A drainage opening 7 is intended for draining urine from the bladder of a user. The drainage opening communicates with a drainage lumen 8 which runs along the shaft. There may be multiple drainage openings in the distal end of the catheter. Preferably each drainage opening communicates with the drainage lumen 8. FIG. 2 shows a cross-section of the shaft on line A-A of FIG. 1, illustrating the lumens 6, 8. At the proximal end of the shaft, the inflation opening communicates with an inflation port 9 and the drainage opening communicates with a drainage port 10. Fluid can be introduced through the inflation port 9 to then pass through the inflation opening 5. Urine received through drainage opening 7 can be collected through drainage port 10. A collecting vessel can be attached to the drainage port.

In the examples shown in the figures, the inflation opening 5 and the drainage openings 7 overlap in the longitudinal axis of the catheter. There could be multiple inflation openings. The or each inflation opening could be distal of the drainage opening, or of a subset of the drainage openings or of all the drainage openings. The or each inflation opening could be proximal of the drainage opening, or of a subset of the drainage openings or of all the drainage openings. Configuring the catheter shaft so that the inflation opening(s) do/does not overlap the drainage opening(s) in a longitudinal direction may help to improve the strength of the shaft.

The entirety of the distal end may taper to the tip, or the distal part of the distal end may taper to the tip; or the distal end may be of constant diameter about the longitudinal axis of the catheter, in which case the tip may be generally hemispherical.

Figure 3:
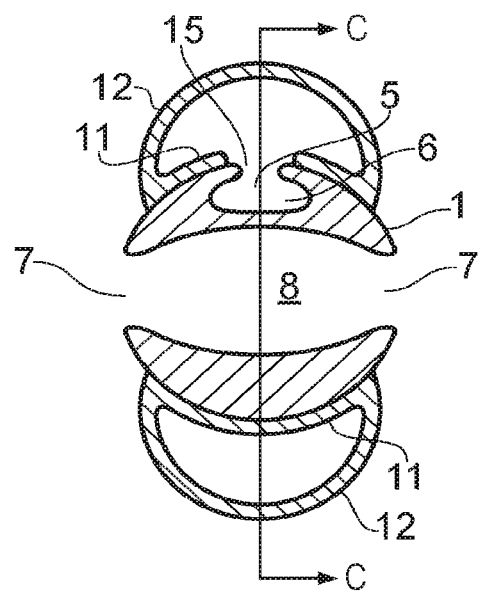
FIG. 3 is a cross-section of the distal part of catheter of FIG. 1 on line B-B, with a partially inflated balloon in place.
Figure 4:
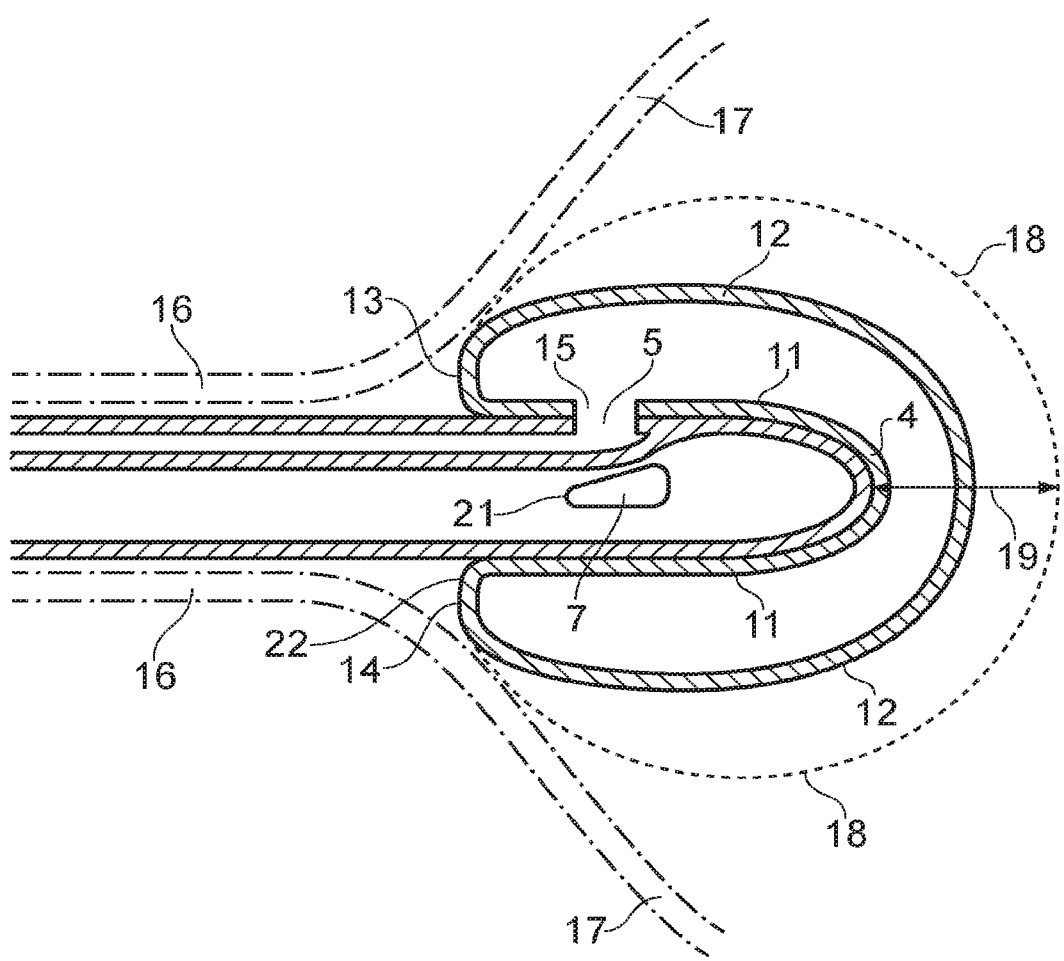
FIG. 4 is a cross-section of the distal part of the catheter of FIG. 1 on the line C-C of FIG. 3, with a partially inflated balloon in place.
Figure 5:
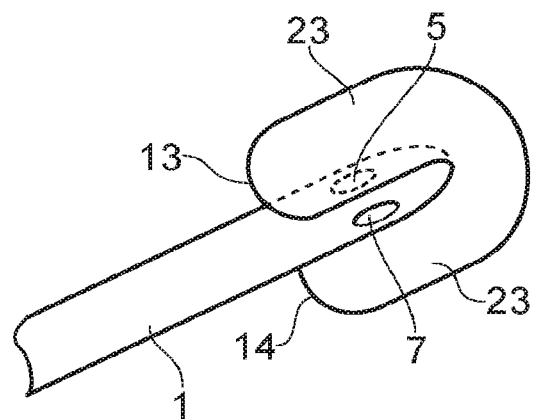
FIG. 5 is an isometric view of the distal part of the catheter of FIG. 1, with a partially inflated balloon in place.

FIG. 3 is a cross-section of the distal part 3 of the shaft on line B-B of FIG. 1, with a partially inflated balloon (not shown in FIG. 1) installed on the shaft. FIG. 4 is a cross-section on line C-C of FIG. 3, and FIG. 5 is an isometric view showing the partially inflated balloon. The catheter of FIG. 2 has two drainage openings 7. The balloon is generally in the form of a tube having an internal wall 11 and an external wall 12. The tube is generally elongate, extending between ends 13, 14. The balloon is made of an elastic sheet material. The tube constitutes a conduit part or all of whose walls are elastic and/or flexible. The balloon is sealed except for an aperture 15 near one of its ends (end 13), by which the interior of the balloon communicates with the inflation opening 5. The balloon is sealed to the shaft 1 of the catheter around the inflation opening. As a result, the balloon can be inflated by introducing fluid such as water or air into the balloon through the aperture 15. The tube-like form of the balloon extends over the tip 4 of the catheter. The balloon is bent around the tip 4. The end 14 of the balloon remote from the aperture 15 is also attached to the distal end of the catheter shaft. This holds the balloon bent over the tip.

FIG. 4 is a cross-section of the distal part of the catheter on line C-C. FIG. 4 shows the balloon in its partially inflated state. FIG. 4 shows in chain-dotted lines the urethra 16 and bladder wall 17 of a person into whom the catheter has been inserted; and dotted line 18 indicates the exterior form of the balloon in its fully inflated state. It should be noted that in its fully inflated state the balloon might be capable of further inflation (i.e. over-inflation). The fully inflated state is the state in which it would normally be left indwelling in a patient's bladder. In its fully inflated state, the size of the balloon, whose outer wall extends radially outward from the shaft of the catheter, resists withdrawal of the catheter through the urethra. This retains the distal end of the catheter in the bladder. The balloon can also form a seal at the base of the bladder to resist leakage of urine past the catheter.

Before the catheter is used, a reservoir containing a predetermined volume of fluid can be engaged with the inflation port. The reservoir could be a syringe or a bag. Once the tip of the catheter is in place in the bladder, the fluid can be squeezed from the reservoir into the balloon. The predetermined volume of fluid can be such as to cause the balloon to be fully inflated when the reservoir is fully evacuated. A valve may be provided exists in the inflation lumen to resist fluid flow in the inflation lumen towards the proximal end of the catheter. This can help the balloon to remain inflated.

As noted above, the balloon is in the form of an elongate tube folded over the tip of the catheter. The ends of the tube are attached to the catheter shaft on either side of the distal end of the catheter. In this example, the attachment points are proximal of, and on either side of, the drainage opening. In other embodiments the attachment points may overlap the drainage opening(s) or be distal to them. The balloon is formed of an elastic sheet material. When the balloon is inflated, the sheet material stretches. This arrangement of the balloon may provide any one or more of the following effects.

1. When the balloon is inflated, the outer skin of the balloon is extended distally of the distal tip 4 of the catheter shaft, along the longitudinal axis of the catheter shaft, as indicated at 19 in FIG. 4. This can help to cushion the wall of a patient's bladder against contact with the tip. The fact that the balloon tube folds over the tip of the catheter means that there are two walls of the balloon overlying the tip. When the balloon is inflated the interior wall of the balloon contacts the tip, forcing the exterior wall to be spaced from the tip.

2. When the balloon is inflated, the inner wall of the balloon is pressed against the tip and the distal side walls of the catheter. Because the exterior of the catheter is convex where it contacts the balloon, the contact between the catheter and the balloon introduces a concavity to the interior wall of the balloon. This engagement between the catheter and the balloon can help to resist the balloon slipping off the tip when the balloon is inflated. This can avoid the need to adhere the balloon to the shaft over the balloon's whole length of contact with the shaft. Preferably the balloon is unadhered to the shaft distally of the most distal point of the or each drainage opening. Preferably the balloon is unadhered to the shaft distally of the most proximal point of the or each drainage opening.

Figure 6:
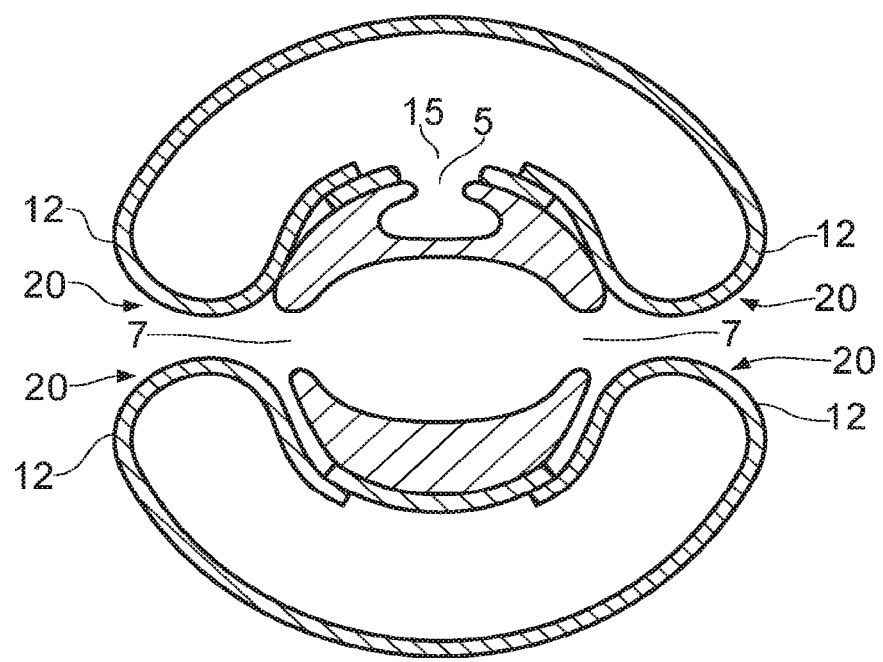
FIG. 6 is a cross-section of the distal part of catheter of FIG. 1 on line B-B, with a fully inflated balloon in place.

3. FIG. 6 is a cross-section of the distal part of the catheter on the plane of FIG. 3, showing the balloon in its fully inflated state. When the balloon is inflated, the outer skin of the balloon is extended laterally of the drainage opening as indicated at 20. This can help to protect the patient's bladder wall against being drawn into the drainage opening. This effect can be promoted by the fact that the balloon tube is attached to the catheter shaft proximally of and on either side of the drainage opening.

4. When the balloon is inflated, the proximal end 21 of the drainage opening 7 is close in the longitudinal direction of the catheter shaft to the most proximal point 22 at which the balloon's outer wall is extended laterally from the catheter shaft. That point is capable of being located substantially at the neck of the bladder. As a result, the drainage opening itself can be located close to the neck of the bladder. This means that there is little scope for undrained urine to pool at the base of the bladder.

Various configurations for the balloon will now be described in more detail.

The balloon has an uninflated state. This may be the balloon's state when the catheter is packaged for supply to a user. The catheter having the balloon applied thereto in its uninflated state may be packaged in a sealed package whose interior is sterile.

In its uninflated state, the balloon may take the form of a tube, for instance a flattened tube, having a greater length than its width. The balloon may be of uniform width, or it may vary in width along its length.

The shaft of the catheter may be formed of a material such as polyurethane, a silicone elastomer or latex. A polyurethane catheter shaft can be more rigid than comparable rubber catheter shafts. This can allow the shaft to have a larger urine carrying capacity without sacrificing rigidity for insertion.

The exterior and/or interior surfaces of the shaft and/or the drainage openings may be coated with a hydrogel coating. Such coatings are produced, for example, by Covalon Technologies Ltd. The application of such a coating to the interior surfaces may result in a smoother interior surface which may reduce encrustation. Alternative coatings may for example contain silver or Nitrofurantoin.

The walls of the balloon may be formed of a material such as polyurethane, a silicone elastomer or latex. The walls of the balloon may be elastic or flexible or both. The walls of the balloon may include one or more regions of greater elasticity and/or flexibility than one or more other regions of the walls. The exterior surface of the balloon may be coated with an antimicrobial agent such as an inert hydromer. The walls may be uniformly elastic across their area, or their Young's modulus may vary across their area. The walls may be uniformly biaxially elastic, or regions of the walls may have different Young's moduli in different directions. Varying the Young's modulus of the walls across their area can allow the shape of the balloon as it expands to be controlled. The walls of the balloon may be of uniform thickness or they may be provided with thickened regions such as ribs. Such thickened regions may influence the shape of the balloon as it expands.

In its uninflated state the balloon extends over the distal tip of the catheter. One or more regions of the balloon may be attached to the shaft of the catheter. One region of attachment may surround the inflation opening 5. The balloon may have an aperture in its wall facing the inflation opening. The aperture may communicate with the inflation opening. In this way the balloon can be sealed around the inflation opening to permit pressure in the balloon to be increased by fluid flow through the inflation opening.

Figure 7:
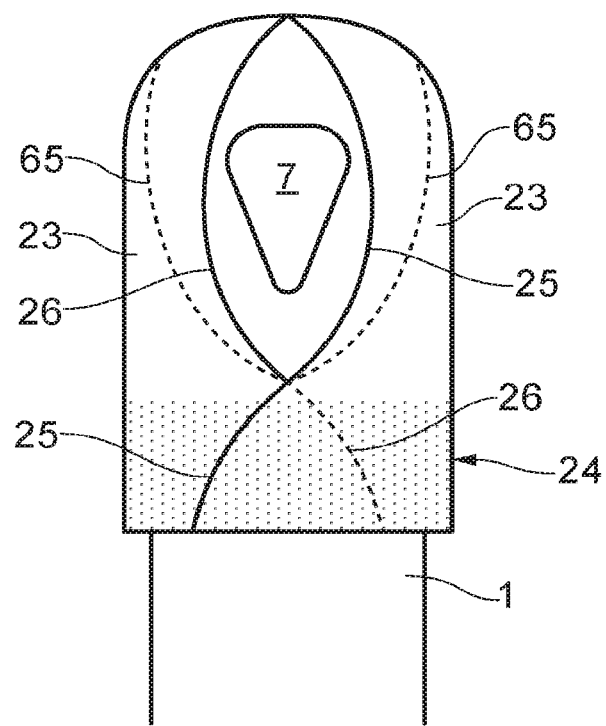
FIG. 7 is a side view of the distal part of catheter of FIG. 1, with an uninflated balloon in place.

In a first configuration, as shown in FIG. 5, the balloon is in the form of a tube which curves over the tip of the catheter. The tube defines legs 23 which extend along the sides of the shaft of the catheter. The balloon is attached to the shaft of the catheter on either side of the tip. Preferably the regions of attachment are diametrically opposite each other with respect to the shaft, but they may be offset. Preferably the regions of attachment are equidistant from the tip of the catheter, but they could be at different distances from the tip. The balloon may be attached to the shaft by adhesive, by welding (e.g. thermal welding) or by a mechanical fixing such as a collar configured to clamp the balloon to the exterior of the catheter shaft. The collar may serve the purpose of securing to the balloon to the shaft. It may be supplemented by adhesive or welding between the balloon and the shaft. The collar may serve the purpose of improving the inflation of the balloon. The collar may surround the balloon proximally of the or each inflation opening, thereby inhibiting inflation of the proximal parts of the balloon. This may improve the shape of the inflated balloon. FIG. 7 illustrates one arrangement. The legs 23 of the balloon are attached to the shaft of the catheter proximally of the drainage opening 7, in region 24. The lateral edge of a first one of the legs is denoted at 25. The lateral edge of the other one of the legs is denoted at 26. In this example, the first leg overlaps the other leg in the region of attachment 24. This can help to promote the balloon adopting, when inflated, a passageway between the edges 25, 26, around the drainage opening, of a size that permits the flow of urine into the drainage opening but is sufficiently small that it helps keep the bladder wall from being drawn into the drainage opening. In another embodiment the two legs of the balloon meet on both sides along the circumference. In another embodiment the two legs meet at opposite edges of one or two urine draining ports. These port(s) might extend more distally than the attachments of the legs to enhance urine drainage.

There may be one, two or more drainage openings. Preferably, there is a drainage opening between each leg of the balloon as it extends along the side of the catheter shaft.

There may be one, two or more inflation openings. The balloon may be inflated from a single end or from more than one end.

It is desirable for the outer surface of the balloon, when the balloon is fully inflated, to have the following properties.
(i) To be spaced from the catheter shaft around the or each drainage opening, to resist the bladder wall being drawn into the drainage openings.
(ii) To define, for the or each drainage opening, a passage located outboard of that drainage opening through which urine can flow from the volume of the bladder into the drainage opening.

It has been found that these characteristics are promoted if the regions where the balloon is adhered to the catheter shaft have any one or more of the following properties:
they are each located wholly or partially proximally of the proximal end of the drainage opening that lies between them;
they overlap proximally of any drainage opening that lies between them.

An arrangement of this type is shown in FIG. 7.

In the catheter of FIGS. 2 to 7 the balloon is an elongate tube which, when folded over the catheter tip has two legs. Alternatively, the balloon may be branched and may have more than two legs extending along the side of the catheter shaft.

Figure 8:
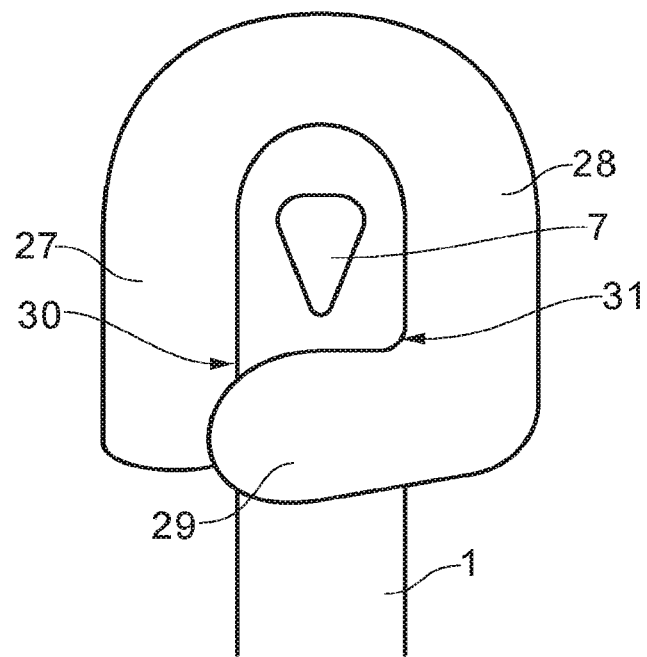
FIG. 8 is an isometric view of the distal part of a catheter with a T-shaped balloon.

In another configuration, as shown in FIG. 8, the balloon is in the form of a T-shaped tube. A central element of the tube curves over the tip of the catheter forming legs 27, 28. At the proximal end of leg 27 the tube has a pair of cross-elements 29. When the balloon is inflated, those cross-elements extend around the shaft 1 of the catheter. The cross-elements can help the inflated balloon to seal around the neck of the bladder. The balloon may be attached to the catheter shaft at locations 30, 31 at the proximal ends of legs 27, 28. Other configurations are possible. Cross-elements could extend from both legs of the balloon. A leg of the balloon could have a single cross-element extending from it.

It is desirable for there to be a relatively small spacing between the proximal end of the balloon, when inflated, and the proximal end(s) of the or each drainage opening. This promotes relatively complete draining of the bladder. To this end, it is preferred that the proximal free region of the outer skin of the balloon (i.e. the proximal part of the outer skin that is not directly adhered to the catheter shaft) is located between 0 and 10 mm proximally of the most proximal part of the or each drainage opening, more preferably between 2 and 8 mm proximally of the most proximal part of the or each drainage opening.

It is desirable for the balloon to resist being dislodged from the tip of the catheter, especially when the balloon is in an inflated state. This may be promoted in a number of ways. First, the balloon may be configured so that in its uninflated state and/or in its fully inflated state each leg of the balloon that extends along the catheter shaft contacts the catheter shaft around an arc of more than 90 degrees about the longitudinal axis of the shaft. In this configuration, the inner surface of the balloon can adopt a concavity about the shaft which physically resists it being dislodged from the shaft. The arc may more preferably be greater than 110 degrees or greater than 130 degrees or greater than 150 degrees. This may be achieved by the respective leg of the balloon being adhered to the shaft around an arc of more than 90 degrees, more than 110 degrees, more than 150 degrees or more than 180 degrees about the longitudinal axis of the shaft. Second, a region of the catheter shaft located longitudinally between the catheter tip and a region of attachment of a part of the balloon may be treated to increase its friction against the balloon. For example, it may be roughened in comparison to the remainder of the catheter shaft, or it may be coated with or formed of a relatively high-friction material such as a rubber. Third, the balloon may be attached to the catheter shaft distally of the drainage opening, e.g. by adhesive or welding. Fourth, it has been found that when the ratio of (i) the mean diameter of the catheter shaft immediately distal of the drainage opening to (ii) the longitudinal distance between the tip of the catheter and the most proximal free region of the outer skin of the balloon is in the region of 1.5:1 the balloon can naturally tend to remain in place on the tip. That ratio may for example be in the range from 1:1 to 2.5:1. To assist this effect, preferably the catheter shaft tapers smoothly toward the tip from the region immediately distal of the drainage opening.

Figure 9:
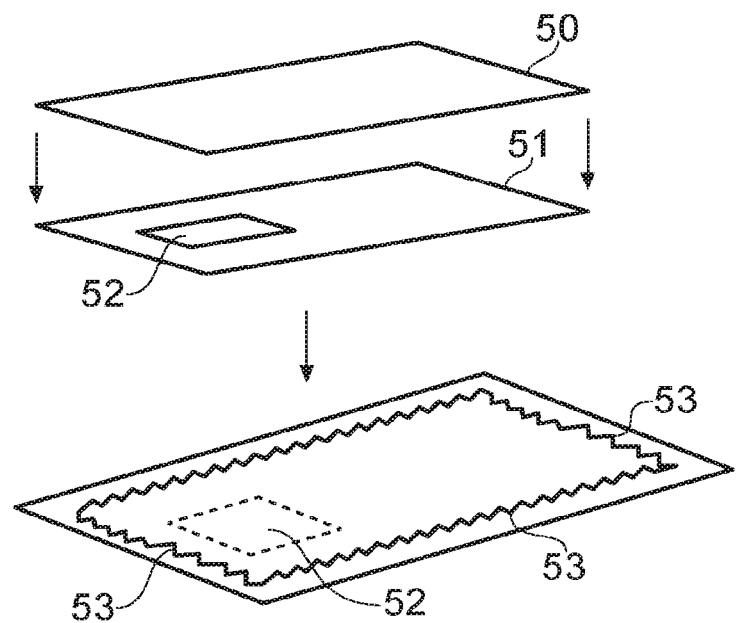
FIGS. 9 and 10 show steps in the manufacture of a balloon for a catheter.
Figure 10:
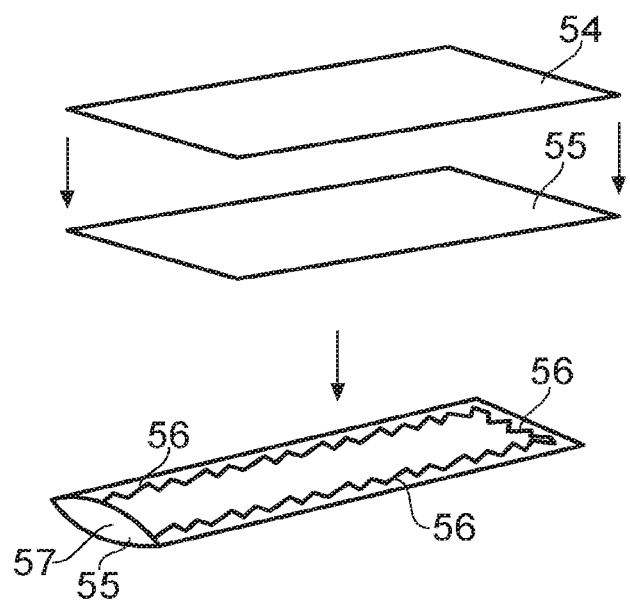

The balloon may be formed from a continuous tube of elastic material. The tube may be extruded or drawn into shape. Alternatively, the tube may be formed of a single sheet of material which is folded so its lateral edges meet, the lateral edges then being joined together. FIGS. 9 and 10 illustrate other ways in which the catheter can be manufactured.

In the method of FIG. 9, the balloon is formed of two sheets 50, 51 of elastic material. Sheet 51 defines an aperture 52. One sheet is placed on top of the other, and the sheets are joined together around their peripheries, as shown at 53. This may be done, for example, by adhesive or by welding. In this example, the sheets are elongate and of uniform width, resulting in the balloon being in the form of a tube of uniform width, but the sheets could be of other shapes. After the sheets, one of which already defines the aperture 52, have been welded together, the balloon is attached to the catheter shaft. The balloon is attached to the shaft by joining the periphery of the aperture 52 to the shaft continuously around the inflation opening 5. This forms a fluid-tight seal between the interior of the balloon and the inflation lumen. The balloon is wrapped over the tip of the catheter and further attached to the shaft on the opposite side of the shaft to the inflation opening.

In the method of FIG. 10, the balloon is formed of two sheets 54, 55 of elastic material. Neither sheet defines an aperture at this stage. The sheets are joined together around their peripheries as indicated at 56, leaving an opening at 57 through which the region between the sheets can be accessed. Then the balloon is attached to the shaft by adhering part of the exterior surface of sheet 55 to the shaft continuously around the inflation opening 5. Then a tool is introduced through opening 57 to pierce the sheet 55 where it overlaps the inflation opening. Then the opening 57 is sealed by joining the sheets 54, 55 together across the opening. This closes the balloon to form a fluid-tight volume except for its connection to the inflation lumen through an aperture pierced by the tool. The balloon is wrapped over the tip of the catheter and further attached to the shaft on the opposite side of the shaft to the inflation opening.

In summary, in the method of FIG. 9 an aperture for communicating with the inflation opening is formed before the balloon is attached to the catheter shaft, and in the method of FIG. 10 an aperture for communicating with the inflation opening is formed after the balloon is attached to the catheter shaft.

In the method described above with reference to FIG. 10, a catheter is provided with an inflation opening, the balloon is attached to the catheter around the inflation opening, and a tool is used to pierce the balloon at the site of the inflation opening. In an alternative process, the catheter may be provided without in inflation opening and the tool may pierce both the balloon and the catheter wall after the balloon has been attached to the catheter.

Thus, in this alternative method, the method may comprise providing a shaft having a proximal end and a distal end, the distal end terminating in a tip, a drainage opening located at the distal end of the shaft, the drainage opening communicating with a drainage lumen of the shaft; providing an elastic-walled conduit having an access opening to the interior thereof; securing a wall of the conduit to the shaft; introducing a tool through the access opening; piercing the wall of the conduit with the tool; piercing the shaft to form an inflation opening located at the distal end of the shaft, the inflation opening communicating with an inflation lumen of the shaft; and closing the access opening.

In a further alternative process, a punch may be used to create not only the access to the inflation lumen through the balloon, but also then to punch a hole in one wall of the balloon. Glue may then be applied around the hole in the balloon and this part of the balloon may be presented to the shaft to secure it.

When the balloon is formed from two sheets of material, they may be sheets of the same material or of different materials. When the sheets are of different materials, they could both be elastic materials, or the sheet forming the inner wall could be a sheet of a relatively inelastic material and the sheet forming the outer wall could be a sheet of a relatively elastic material.

Ways in which the balloon can be provided in its uninflated state will now be described.

Figure 11:
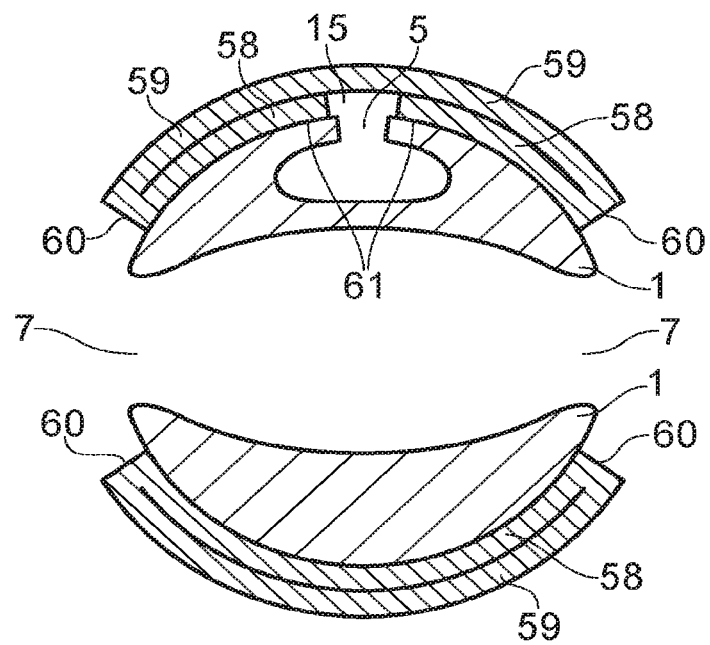
FIG. 11 is a cross-section of the distal part of catheter of FIG. 1 on line B-B, with an uninflated balloon of a first design in place.

FIG. 11 is a cross-section at line B-B of FIG. 1 with an uninflated balloon in place on the catheter shaft. In this example the balloon is pressed against the shaft so as to define an inner wall 58 and an outer wall 59. Inner wall 58 can be affixed to the catheter shaft. The walls are joined together along their lateral edges, as indicated at 60. The inner wall is sealed to the shaft around the inflation opening at regions 61.

Figure 12:
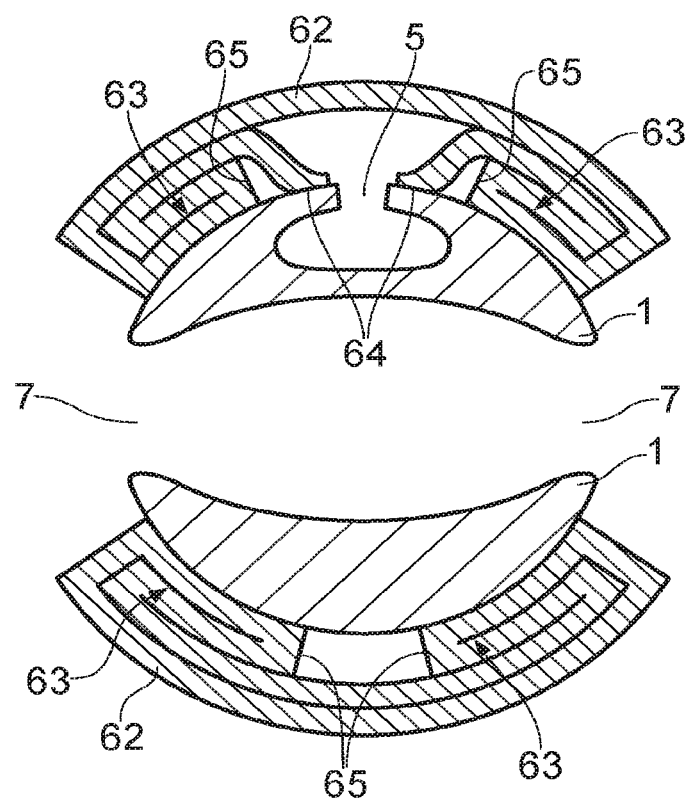
FIG. 12 is a cross-section of the distal part of catheter of FIG. 1 on line B-B, with an uninflated balloon of a second design in place.

FIG. 12 is a cross-section on an analogous plane to FIG. 11. FIG. 12 shows a balloon whose lateral edges are folded under the outer layer of the balloon. The outermost layer of the balloon in its uninflated state is indicated at 62. The lateral edges 63 of the balloon are folded away from the outermost layer 62. The lateral edges are located between the outer layer 62 and the catheter shaft 1. The lateral edges comprise two layers of the balloon. As a result, when the balloon is inflated, the lateral edges expand out from under the outermost layer 62. This can allow the balloon more freedom to expand than in the arrangement of FIG. 11. Providing additional balloon material in this way can allow the balloon to adopt a larger size than it would otherwise do for a given degree of stretch. In the arrangement of FIG. 12, there are more than two thicknesses of the material of the balloon at some points overlying the catheter stem. The balloon is sealed to the shaft around the inflation opening at regions 64.

FIG. 7 shows a balloon having this folded-under configuration. If can be seen from FIG. 12 that the folded-under lateral edges 63 terminate at their central ends at fold lines 65. Those fold lines are shown in FIG. 7. As indicated in FIG. 7, the width of the portion of the balloon that is folded under the outermost layer may increase towards the tip of the catheter shaft. It has been found that this is helpful in promoting a desirable form of balloon in its inflated state.

Figure 13:
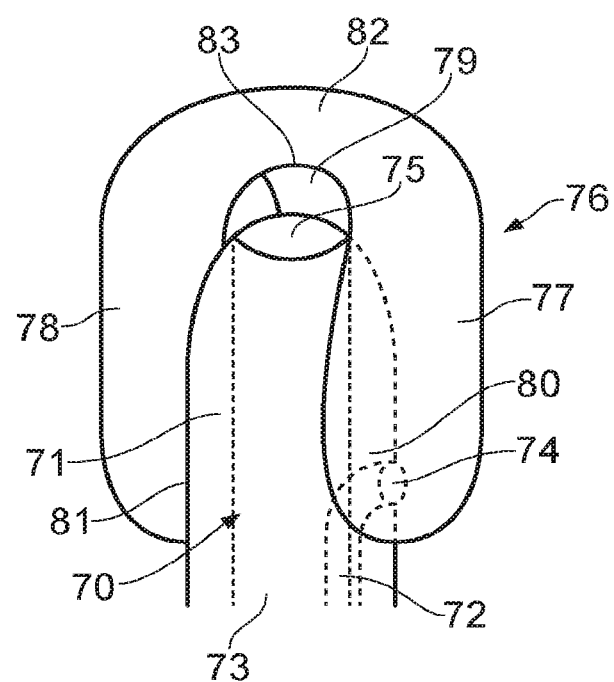
FIG. 13 is an isometric view of an alternative embodiment of catheter.

FIG. 13 shows an alternative embodiment of urinary balloon catheter with the balloon in its inflated state. The distal end of the catheter is shown generally at 70. The shaft 71 of the catheter comprises an inflation lumen 72 and a drainage lumen 73. These extend along the shaft of the catheter towards the proximal end in the same way as is shown in FIG. 1. At the distal end, the inflation lumen terminates in an inflation opening 74 and the drainage lumen terminates in a drainage opening 75. A balloon indicated generally at 76 is located at the distal end of the catheter. The balloon is configured so as to have multiple side channels 77, 78, 79 which, when inflated, will run in the longitudinal direction of the catheter from a respective attachment point 80, 81 on the shaft of the catheter proximally of the tip to a region 82 where the channels join and intercommunicate. At least one of the channels (in this example that is channel 77) communicates with the or an inflation port. The proximal ends of the channels are sealed. The or each channel through which inflation can take place is sealed around the respective inflation opening. The balloon is configured so that the intercommunication region 82 is located distally of the tip of the catheter. In one example, the side channels may be configured such that when the balloon is inflated the interior wall 83 of the material defining the intercommunication region 82 contacts the tip of the catheter. In that case the drainage opening may be located in the side of the catheter shaft, as for the embodiments of FIGS. 1 to 12. Alternatively, the side channels may be configured such that when the balloon is inflated the interior wall 83 of the material defining the intercommunication region 82 is spaced from the tip of the catheter. This is shown in FIG. 13. In this case, the drainage opening may be located at the tip of the catheter, as shown in FIG. 13. This drainage opening is located in the tip of the catheter. The drainage opening opens distally from the tip. This may have a number of advantages. Locating the drainage opening at the tip of the catheter may allow for cheaper manufacturing because the drainage lumen can simply run longitudinally along the catheter shaft. A drainage opening at the tip of the catheter may be less prone to encrustation around the opening. The channels extend laterally from the catheter shaft and may help to keep bladder mucosa from contacting the shaft. There may be two, three or more side channels. In its uninflated state, the balloon may be draped or stretched over the tip of the catheter, retained by the attachment points 80, 81.

The balloon may initially adopt an uninflated state. In its uninflated state the exterior surface of the balloon may conform closely to the exterior surface of the catheter. That may facilitate inserting the catheter into the bladder of a user. In the uninflated state, the balloon may be taut against the exterior surface of the catheter. In the uninflated state, material of the balloon may be packaged in the drainage lumen. For example, in the uninflated state of the balloon of FIG. 13, material of the intercommunication region 82 may reside in the drainage lumen having been passed through the drainage opening. This can allow free material of the balloon in its uninflated state to be held so that it is not loose externally of the catheter. That may assist insertion of the catheter into a user. In the example of FIG. 13, the diameter of the drainage opening may be greater than 50% of the mean diameter of the catheter shaft and/or of the mean diameter of that part of the catheter shaft distally of the most proximal point of attachment of the balloon to the catheter shaft.

In any of the embodiments, the outer surface of the catheter shaft may define a recess in which the uninflated balloon can sit. The recess may be sized so that the exterior of the uninflated balloon lies flush with the exposed surface of the catheter. This may help the catheter to be inserted through the urethra.

The material of which the balloon is formed may have a tendency to self-adhere, which can help to keep it in its folded and/or compressed state until it is inflated. This may help the catheter to be inserted through the urethra.

In any of the embodiments, additional layers of material may be provided over the balloon. For example, an additional web may be provided over the balloon in order to smooth the exterior surface of the catheter's distal end when the balloon is inflated. Alternatively, or in addition, there could be a further balloon located distally and/or laterally outward of the balloons described above.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A catheter comprising:
   a shaft having a proximal end and a distal end, the distal end terminating in a tip;
   a drainage opening located at the distal end of the shaft and on a side of the shaft, the drainage opening communicating with a drainage lumen of the shaft;
   a balloon located at the distal end of the shaft;
   wherein at least part of the balloon is in the form of an elongate tube, the elongate tube being folded over the tip.

2. A catheter as claimed in claim 1, wherein the balloon comprises a first region secured to the shaft, a second region secured to the shaft, and an elastic-walled and/or flexible-walled conduit extending between the first region and the second region.

3. A catheter as claimed in claim 2, wherein at least part of the first region and at least part of the second region are located proximally of the drainage opening, and the first region is at one end of the tube and the second region is at the other end of the tube.

4. A catheter as claimed in claim 2, wherein the first and second regions overlap.

5. A catheter as claimed in claim 2, wherein the first region spans an arc of greater than 90 degrees around the longitudinal axis of the catheter.

6. A catheter as claimed in claim 2, wherein the first region spans an arc of greater than 180 degrees around the longitudinal axis of the catheter.

7. A catheter as claimed in claim 2, wherein the ratio of (i) the mean diameter of the catheter shaft immediately distal of the drainage opening to (ii) the distance from the most distal part of the first region to the tip of the catheter is in the range from 1:1 to 2.5:1.

8. A catheter as claimed in claim 2, wherein the balloon is secured to the shaft at the first and second regions by a mechanical fixing.

9. A catheter as claimed in claim 1, wherein when the balloon is in an uninflated state:
   the tube has lateral edges;
   the balloon comprises an outer layer defining the exterior of the balloon in the uninflated state; and
   the balloon is folded so that the lateral edges are located between the outer layer and the shaft of the catheter.

10. A catheter as claimed in claim 1, wherein the catheter comprises an inflation opening located at the distal end of the shaft, the inflation opening communicating with an inflation lumen of the shaft and with the interior of the balloon.

11. A catheter as claimed in claim 10, wherein the balloon comprises two or more walls where it extends over the tip, and the region between the walls communicates with the inflation opening.

12. A catheter as claimed in claim 1, wherein the balloon is configured such that when inflated an exterior wall of the balloon is located distally of and spaced from the tip of the catheter.

13. A catheter as claimed in claim 1, wherein the balloon is configured such that when inflated an interior wall of the balloon bears against the tip of the catheter.

14. A catheter as claimed in claim 1, wherein the drainage opening is located on a side of the catheter shaft and the balloon is configured such that, when inflated, regions of the exterior of the balloon are located laterally outward of that side of the catheter shaft on either side of the drainage opening.

15. A catheter as claimed in claim 1, wherein the balloon is configured such that, when inflated, regions of the exterior of the balloon are located radially outward of the catheter shaft proximally of the most proximal part of the drainage opening.

16. A catheter as claimed in claim 1, wherein the balloon is formed of a material that has a tendency to adhere to itself.

17. A catheter as claimed in claim 1, wherein the material forming the wall of the balloon is of uniform elasticity across its area.

18. A catheter as claimed in claim 1, wherein the material forming the wall of the balloon is of non-uniform elasticity across its area.

19. A catheter as claimed in claim 1, wherein:
the balloon is configured so that when the balloon is inflated, a wall of the balloon facing the tip is spaced from the tip; and
the drainage opening opens distally from the tip.

20. A catheter as claimed in claim 1, wherein:
the balloon is in its uninflated state; and
material of the balloon is stowed in the drainage lumen.

\* \* \* \* \*